United States Patent [19]

Piunti

[11] Patent Number: 5,724,996
[45] Date of Patent: Mar. 10, 1998

[54] METHOD FOR CONTROLLED STIMULATION OF PREDETERMINED PARTS OF THE HUMAN BODY BY APPLICATION OF VARIABLE ELECTRIC SIGNALS

[75] Inventor: Luigi Piunti, Porto D'Ascoli, Italy

[73] Assignee: Galaxy-Top International S.p.A., Benedetto del Tronto, Italy

[21] Appl. No.: 749,468

[22] Filed: Nov. 15, 1996

[51] Int. Cl.⁶ ..................................................... A61N 1/36
[52] U.S. Cl. ..................................................... 128/898
[58] Field of Search .................................. 607/46, 48, 67, 607/72; 128/898

[56] References Cited

U.S. PATENT DOCUMENTS 5,433,737  7/1995  Aimone ........................................ 607/72

*Primary Examiner*—Scott M. Getzow
*Attorney, Agent, or Firm*—McAulay Fisher Nissen Goldberg & Kiel, LLP

[57] ABSTRACT

A method for controlled stimulation of predetermined parts of the human body, includes application of a plurality of positive electrodes and a plurality of discharge electrodes, a voltage being then applied to the positive electrodes and discharge electrodes and varied in frequency and intensity according to a predetermined way. In accordance with the method a plurality of configurations of the positive electrodes and discharge electrodes are adopted in peripheral positions of body zones to be stimulated, and the electrodes are activated in prefixed sequences so as to provoke in these zones concentration of electromagnetic waves which improve some physiological parameters.

10 Claims, 8 Drawing Sheets

METHOD FOR CONTROLLED STIMULATION OF PREDETERMINED PARTS OF THE HUMAN BODY BY APPLICATION OF VARIABLE ELECTRIC SIGNALS

FIELD OF THE INVENTION

The present invention relates to stimulation of parts of the human body, mainly for improvement of muscles tone and lymphatic and blood circulation, as well as for improving a person's aesthetic appearance.

In particular, the present invention concerns a method of controlled stimulation of predetermined body zones by application of electric signals of variable intensity.

DESCRIPTION OF THE PRIOR ART

It is known that stimulation of predetermined zones of the human body, by suitable techniques, is undeniably advantageous, above all for improvement of muscle tone and blood circulation in these zones under treatment.

The stimulation is usually performed mechanically or manually, by massages executed by suitably instructed people.

The mechanical stimulation is carried out by machines that in fact substitute the massager's hands with vibrating belts or discs, or with light electric discharges applied to the ends of the muscles bands by suitably placed groups of electrodes.

Italian Paten application No. BO94A000254, of the same Applicant, discloses a method for improving the muscles tone and blood circulation by application of an electric voltage, modulated in such a way as to form predetermined sequences of particular wave forms, whose intensity and duration are defined in relation to suitable programs, customized for each single application.

The above mentioned methods and apparatuses for electric/mechanical stimulation of the human body act on the muscles bands to provoke their subsequent contractions and pulling, which simulate stresses deriving from a prolonged physical activity thus contributing to improvement of their tone.

In particular, the apparatuses for electric stimulation use couples of electrodes placed on opposite extremities of the muscle bands to maximize application effects.

SUMMARY OF THE INVENTION

The main object of the present invention is to propose a method for controlled stimulation of predetermined parts of human body that allows not only to improve muscles tone and blood circulation, but also to facilitate the disposal of excessive liquids and melting of possible localized adipose substances.

Another object of the present invention is to obtain the above mentioned results in a simple, easy for the user way, and extremely repetitive.

The above mentioned objects are obtained in accordance with the contents of the claims. dr

BRIEF DESCRIPTION OF THE DRAWINGS

The characteristic features of the proposed method will be pointed out in the following description with reference to the enclosed drawings, in which.

DESCRIPTION OF THE PREFERRED EMBODIMENT

Figure 1:
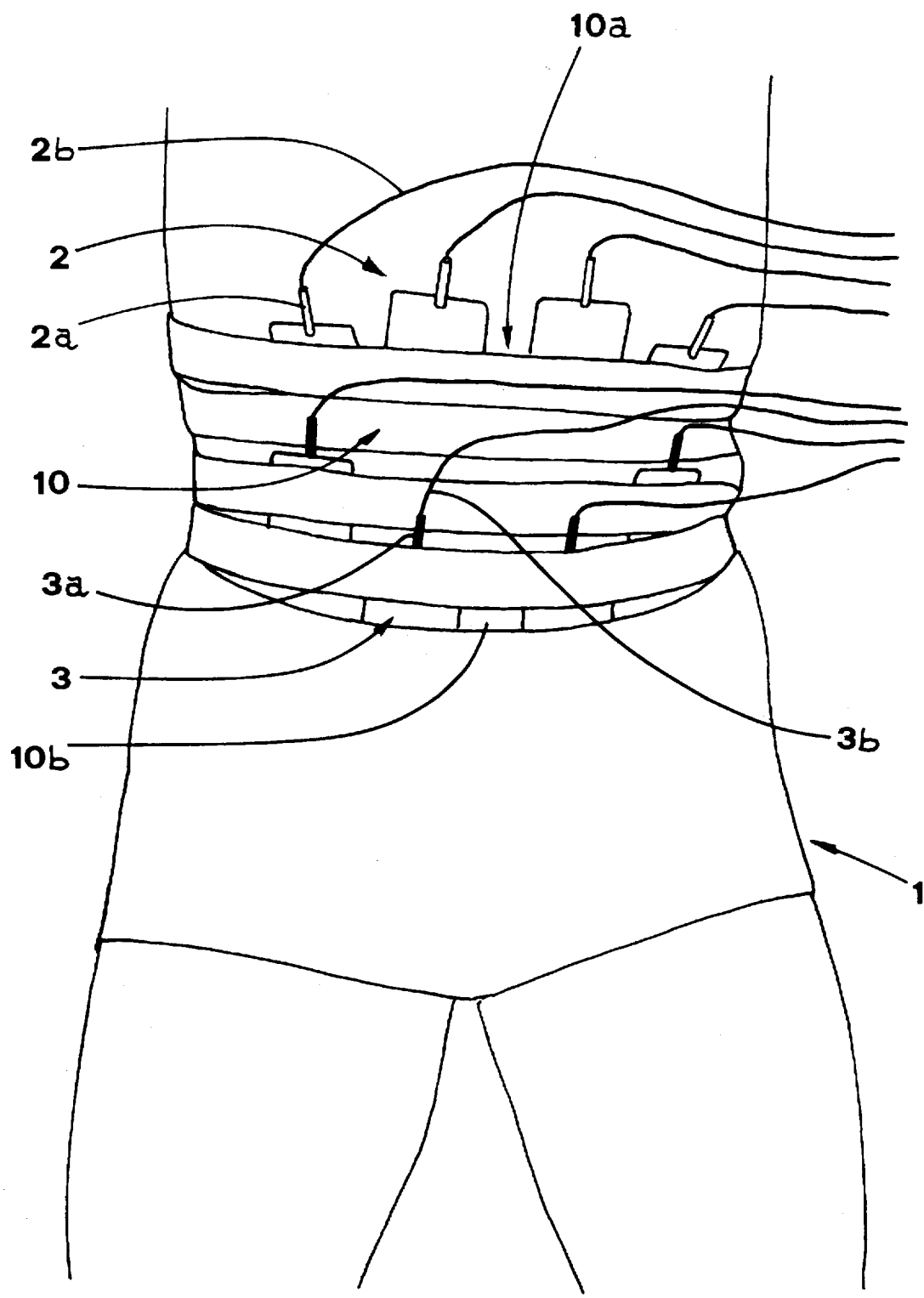
FIGS. 1 and 2 show two configurations of the electrodes, according to the method being the subject of the present invention, aimed at abdomen reduction.

With reference to the above mentioned figures, numeral 2 indicates a plurality of electrodes, of known type and easily available on the market. The electrodes are applied in predetermined points situated on the user 1 skin.

These electrodes 2 are connected by respective clamps 2a and electric cables 2b with an apparatus similar to e.g. the one disclosed in the Italian patent application No. BO94A000254 of the same Applicant.

The electrodes 2 generally correspond to the positive polarity of electric voltage generated by the apparatus.

For sake of clarity, the clamps 2a are distinguished by light color.

Likewise, numeral 3 indicates a plurality of electrodes which generally correspond to the negative or discharge polarity generated by the same apparatus, to which the electric cables 3b are connected by means of clamps 3a which can be distinguished because of their dark color.

According to the method in question, a plurality of the above mentioned positive electrodes 2 and discharge electrodes 3 are first placed peripherally with respect to the body areas 10, 20, 30, 40, 50, and afterwards, activated by the above mentioned stimulation apparatus for predetermined time intervals.

The apparatus generates electric signals of variable frequency and intensity, according to predetermined sequences, that provoke in the body areas 10, 20, 30, 40, 50 concentration of electromagnetic waves for improvement of some physiological parameters of the same human body.

The main involved physiological parameters depend directly on the configuration of the positive electrodes 2 and the discharge electrodes 3, which therefore is extremely important for performing the present method.

The positive electrodes 2 are always applied to the peripheral areas 10a, 20a, 30a, 40a, 50a of the said areas 10, 20, 30, 40, 50 which are closer to the heart, while the discharge electrodes 3 are always applied to the peripheral areas 10b, 20b, 30b, 40b, 50b of the areas 10, 20, 30, 40, 50 which are farther from the heart.

The main configurations of the electrodes will be now described.

With particular reference to FIG. 1 illustrating a first configuration, there are four positive electrodes 2, substantially shaped like a squashed semicircle with a convex part turned upwards and applied to a lower abdomen area 10, directly over the navel.

According to this configuration, there are four discharge electrodes 3, substantially arranged to form a squashed semicircle with a convex part turned downwards and applied to the same abdomen area 10, directly over the pubis.

With the electrodes applied according to this first configuration, the lower part of the user's 1 abdomen is stimulated and thus its reduction is facilitated by continuous draining of excessive liquids and melting of adipose substances.

Another result is increase of the muscles tone.

Figure 2:
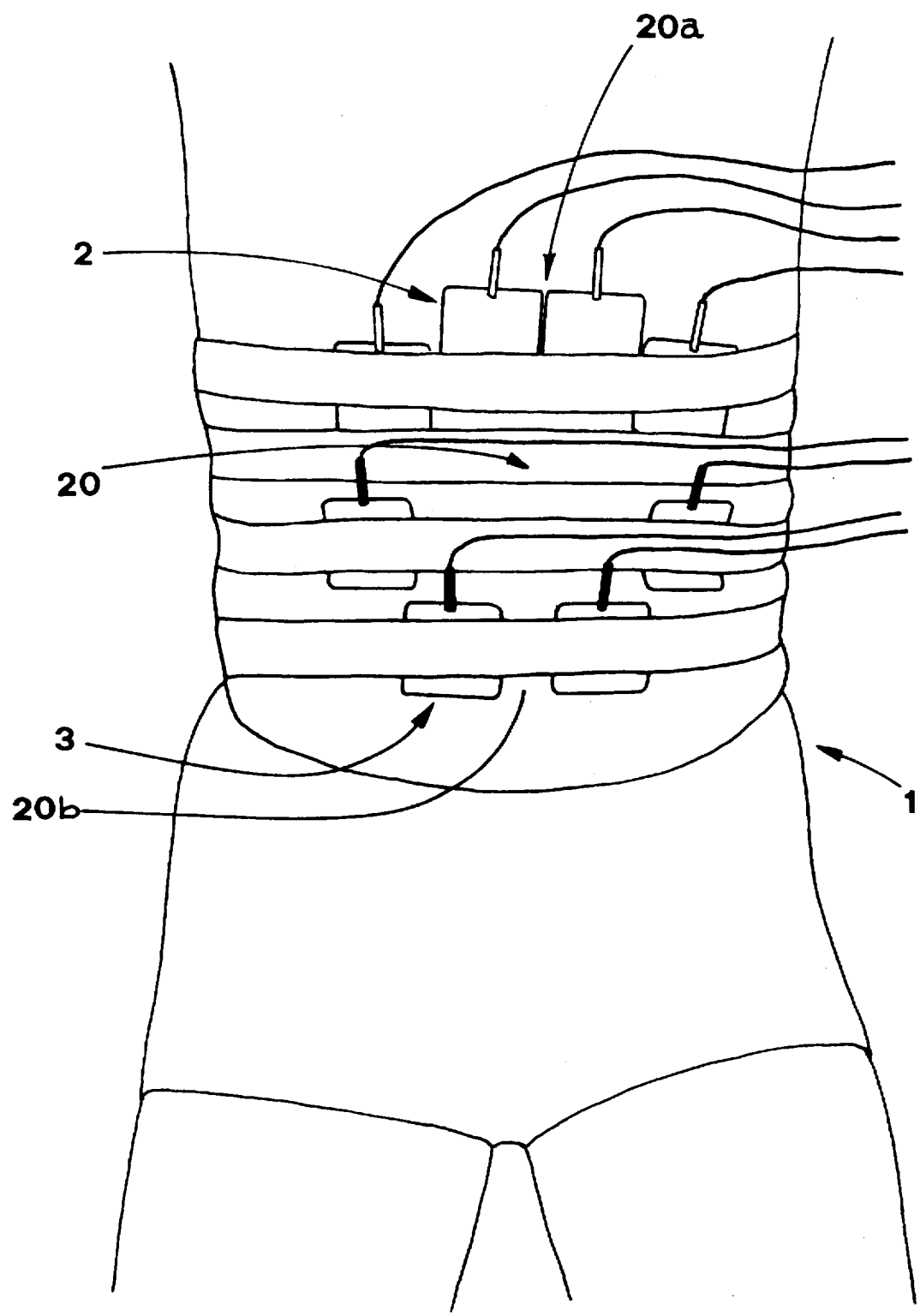

With reference to FIG. 2 illustrating a second configuration, there are four positive electrodes 2, substantially arranged to form a squashed semicircle with a convex part turned upwards and applied to an upper abdomen area 20, directly below the chest, and four discharge electrodes 3, substantially arranged like a squashed semicircle with a convex part turned downwards and applied directly over the navel.

This second configuration allows to stimulate the upper part of the user's 1 abdomen in exactly the same way as already described in the first configuration.

Figure 3:
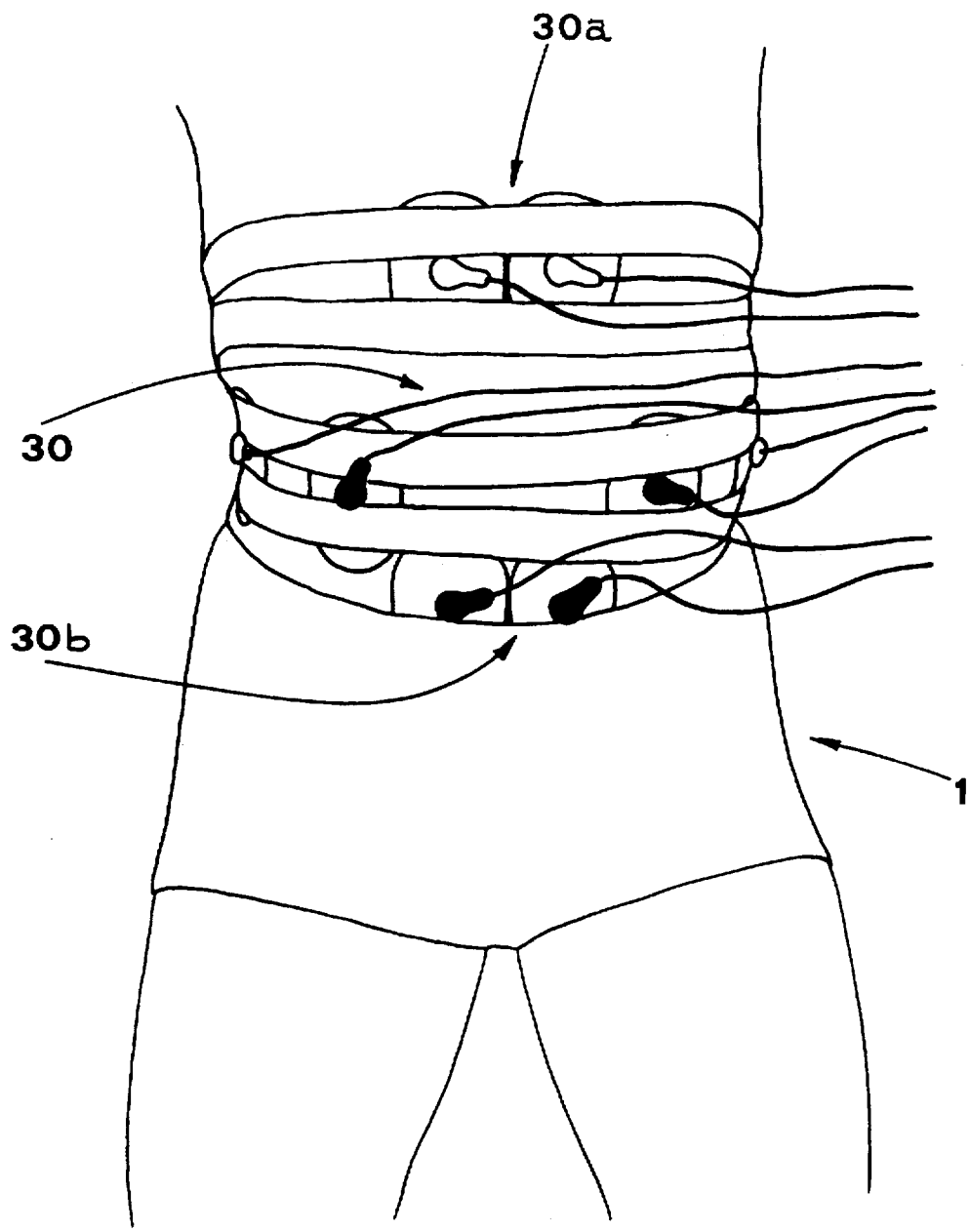
FIG. 3 shows an electrodes configuration for improvement of abdomen muscles tone.

With reference to FIG. 3 illustrating a third configuration, the positive electrodes 2 and the discharge electrodes 3 are arranged vertically symmetrical around an abdomen area 30.

The positive electrodes 2 are applied to the oblique rectus muscle joint and the discharge electrodes 3 are applied to the lower part of the abdomen rectus muscle.

The stimulation with electrodes 2, 3 applied according to this third configuration facilitates first of all improvement of muscles tone in the abdomen area.

Figure 4:
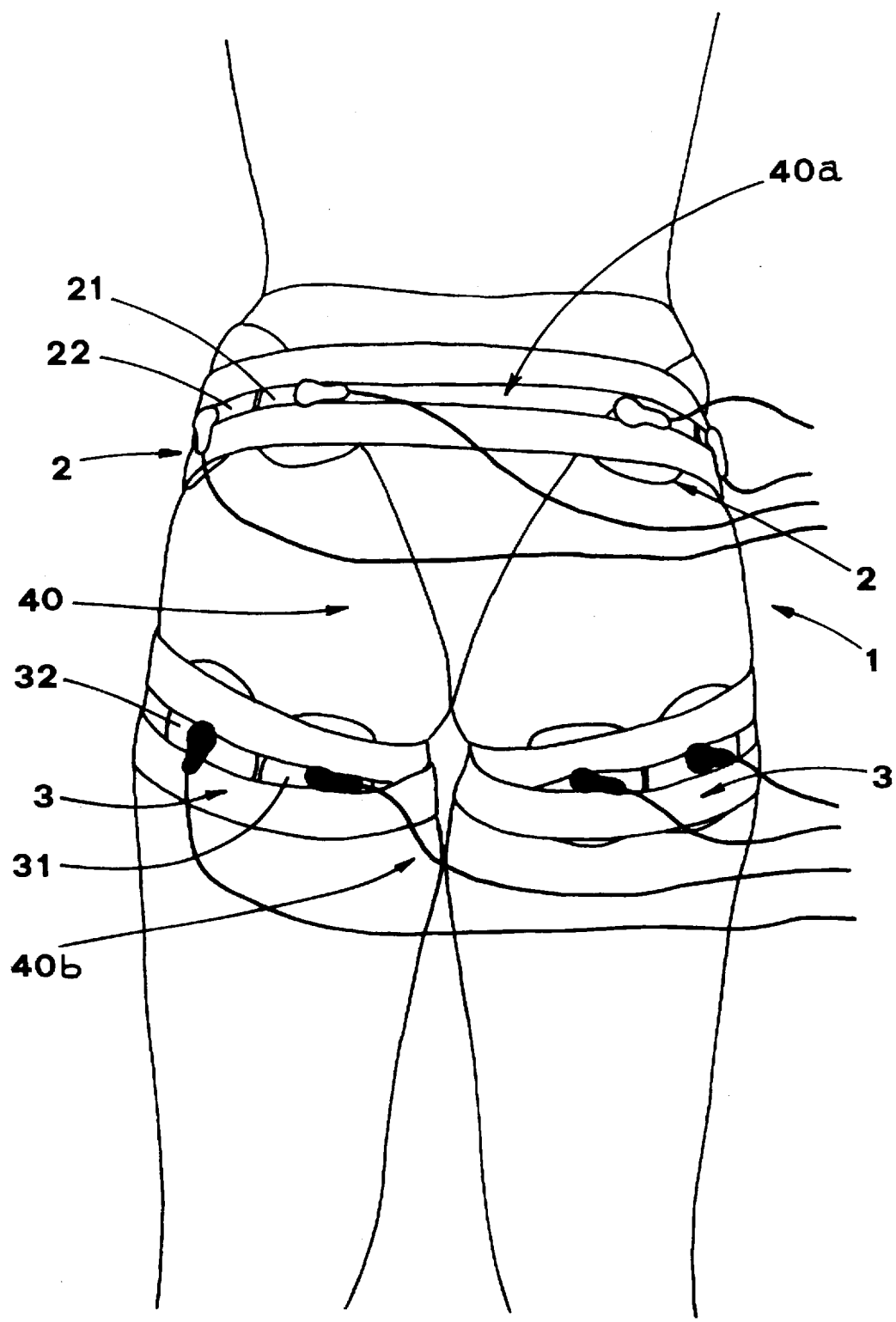
FIG. 4 shows an electrodes configuration for improvement of gluteal muscles tone.

With reference to FIG. 4 illustrating a fourth configuration, the positive electrodes 2 and the discharge electrodes 3 are arranged around a gluteus area 40, more precisely in correspondence to the medium and big gluteus.

A first positive electrode 21 is applied, in a substantially central position, directly over each of the gluteus areas 40 and a second positive electrode 22 is applied beside the first electrode 21 to the external part of the gluteus 40.

A correspondent couple of discharge electrodes 31, 32, first and second respectively, are applied directly below the gluteus area 40.

The stimulation performed according to a suitably defined sequences and with electrodes 2, 3 applied according to the above described configuration, allows to improve muscles tone of the gluteus 40 area.

Figure 5:
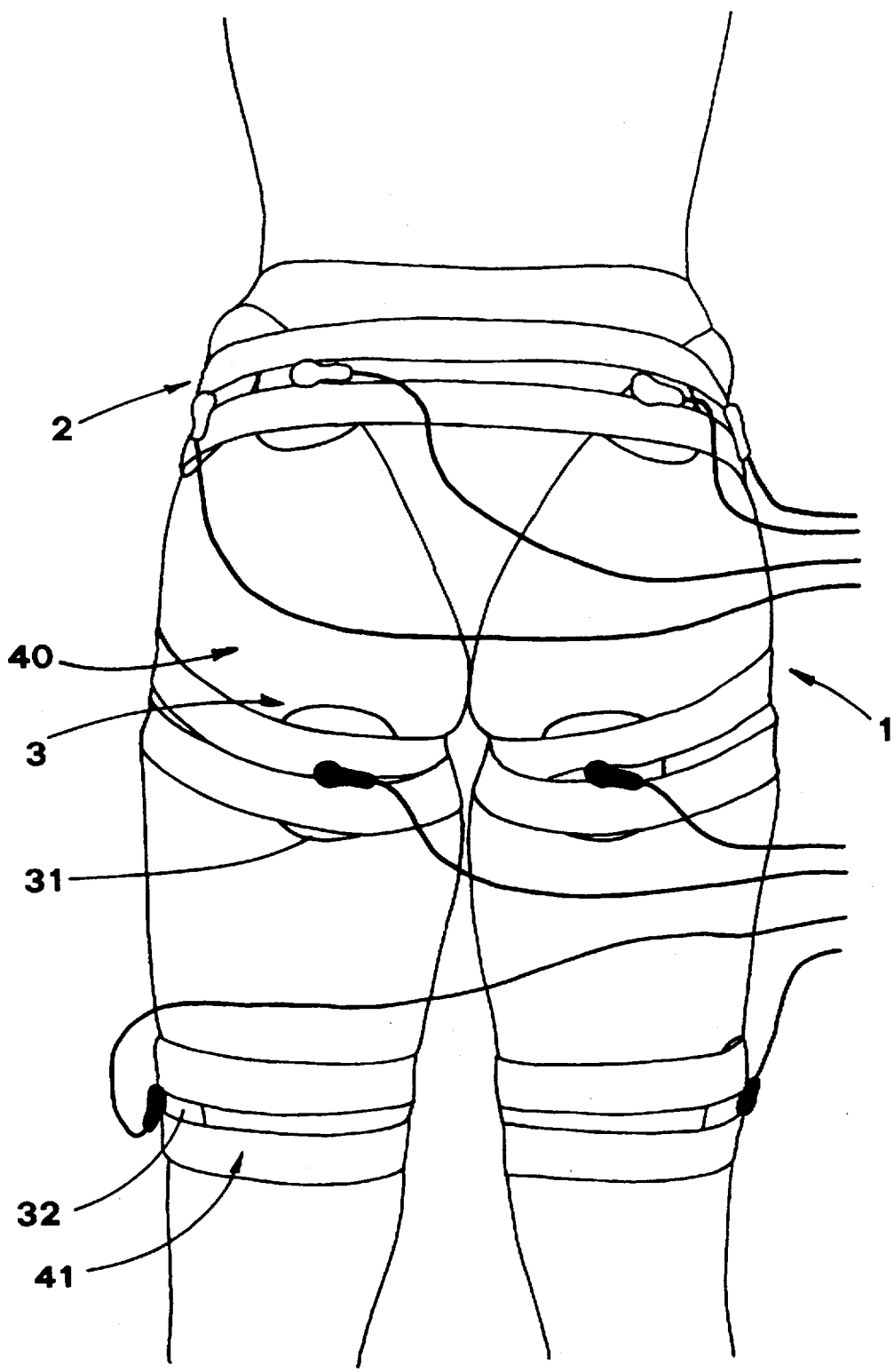
FIG. 5 shows an electrodes configuration particularly aimed at gluteus and external thigh reduction.

With reference to FIG. 5, illustrating a fifth configuration, for each gluteus area 40, the second discharge electrode 32, as described in the previous fourth configuration, is moved to the external part 41 of the leg, directly over the knee.

Besides the results of the stimulation with the electrodes 2, 3 applied according to the fourth configuration, also reduction of the excessive substances in the gluteus and external thigh areas are obtained by the stimulation according to the fifth configuration.

Figure 6:
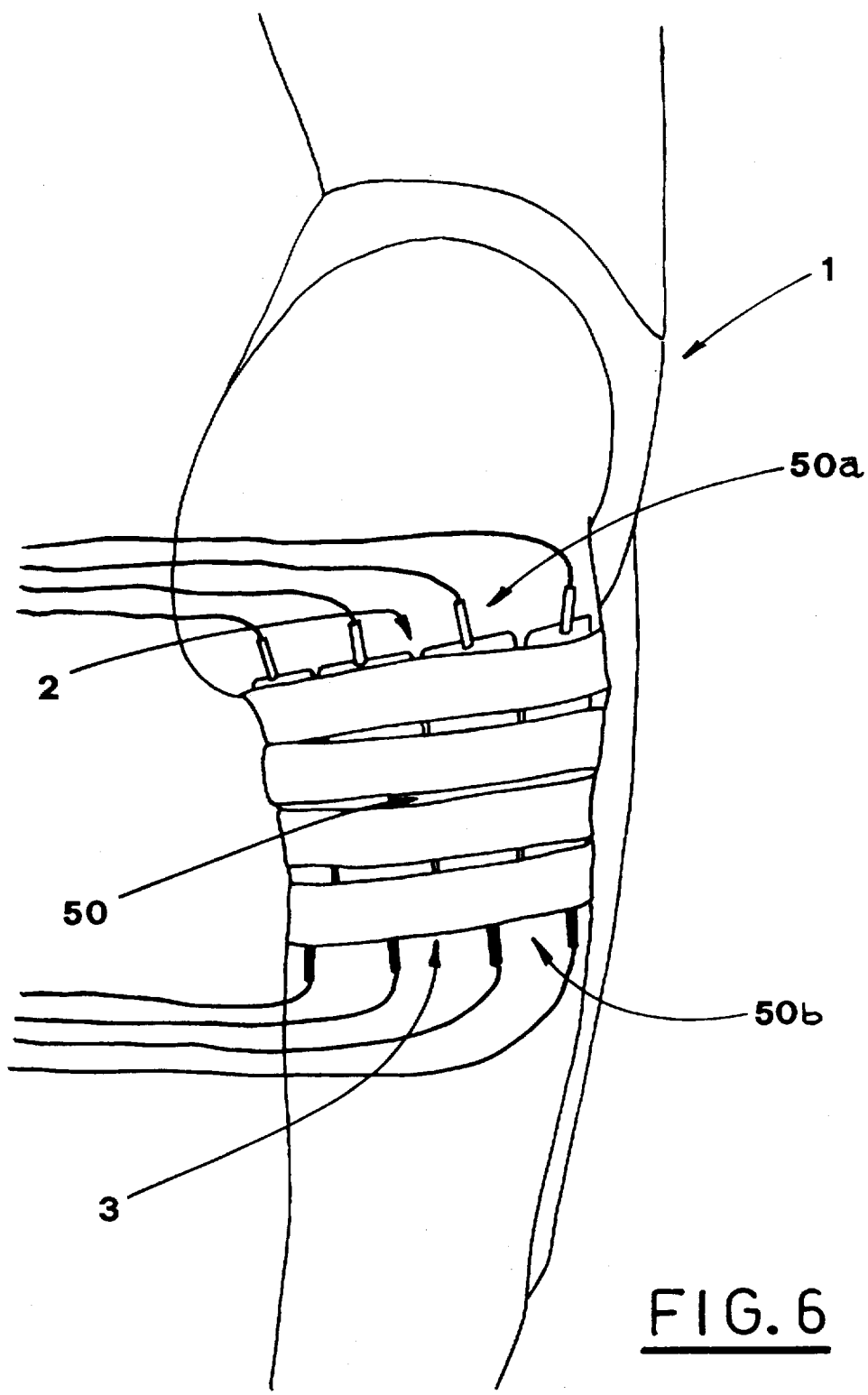
FIG. 6 shows an electrodes configuration for external thigh reduction.

With reference to FIG. 6, illustrating a sixth configuration, four positive electrodes 2, arranged horizontally side by side, are applied directly over the external thigh area 50, and four discharge electrodes 3, arranged horizontally side by side, are applied directly below the external thigh area 50.

The electric stimulation performed on the external thigh area according to a suitable program and with the electrodes 2, 3 applied as in the sixth configuration, allows to considerably reduce excessive liquids and adipose substances in this area.

Figure 7:
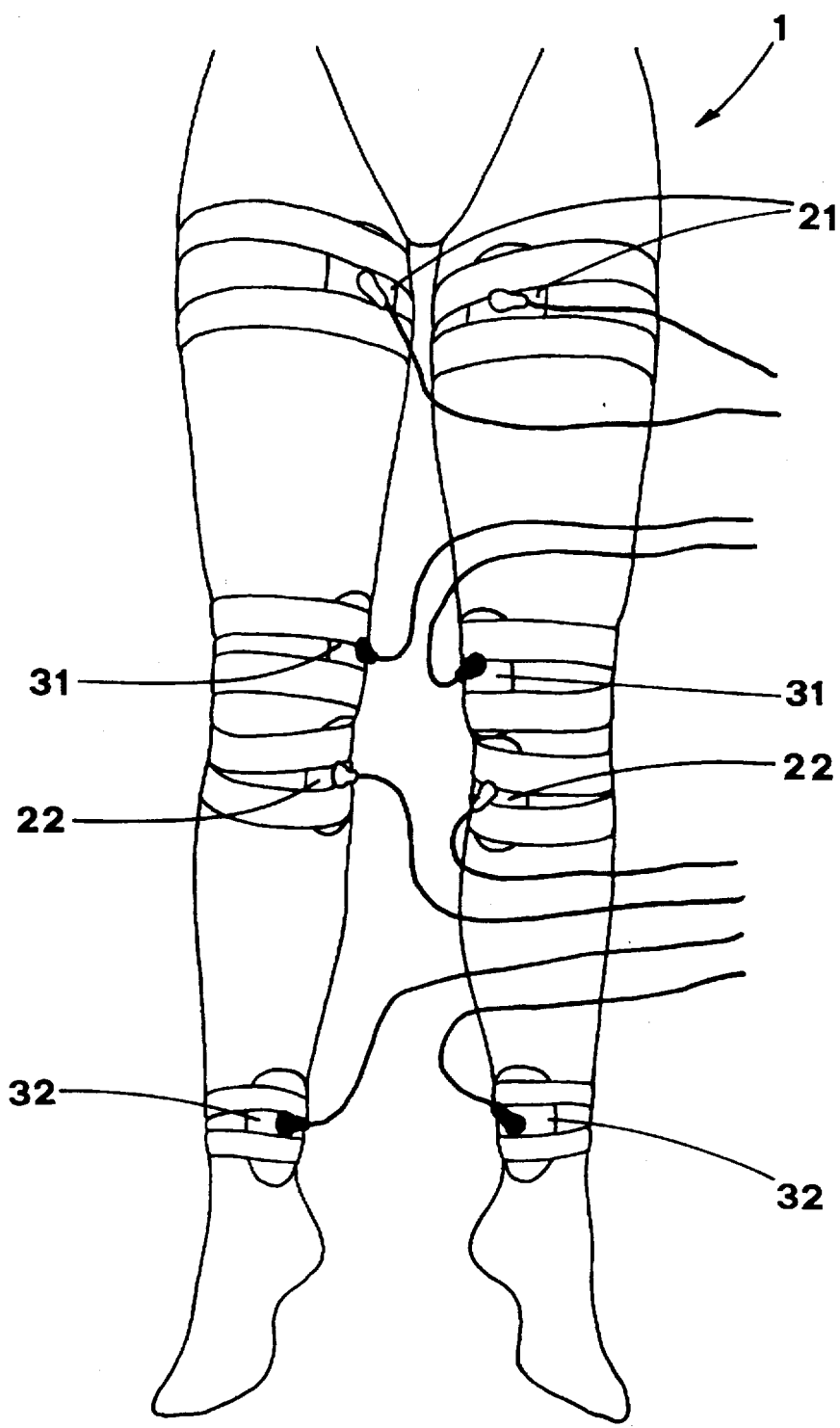
FIGS. 7 and 8 show electrodes positions near drain points, defined by acupuncture techniques.
Figure 8:
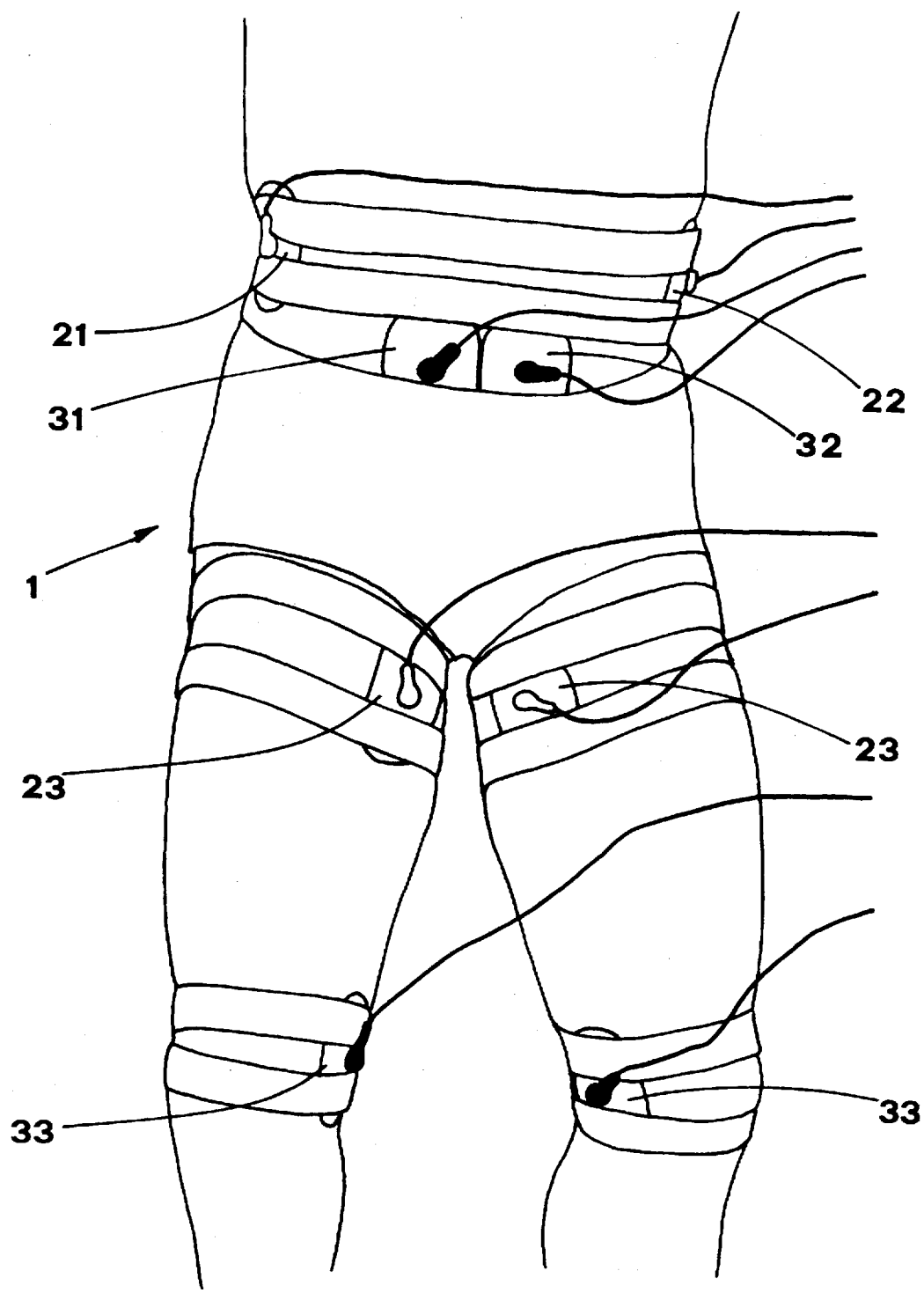

With reference to FIGS. 7 and 8, illustrating seventh and eighth configurations, the groups of positive electrodes 2 and discharge electrodes 3 are applied to drain points defined according to the acupuncture technique.

In particular, according to the seventh configuration, a couple of positive electrodes 21, 22 are applied to the internal thigh area and to the lower part of the internal knee area, and a couple of discharge electrodes 31, 32 are applied to the upper part of the internal knee area and to the internal part of the ankle.

The above described configuration of the electrodes allows to improve blood and lymph circulation in the legs area.

According to the eighth configuration, a couple of positive electrodes 21, 22 are applied to the oblique rectus muscles joint, a corresponding couple of discharge electrodes 31, 32 are applied symmetrically to the lower part of the abdomen rectus muscle.

Another positive electrode 23 is applied to the upper part of each internal thigh area and another discharge electrode 33 is applied to the internal knee area.

The electric stimulation with electrodes applied according to the last configuration reduces the abdomen in the region of the oblique abdomen muscles and drains excessive liquids in the lower limbs area.

The main advantage of the present invention derives from the fact that it provides a method for controlled stimulation of predetermined parts of the human body that allows to perform individualized programs of such stimulation.

These programs non only guarantee harmonious improvement of the muscles tone and blood circulation in the treated areas, but also facilitates draining of excessive liquids and melting of localized adipose substances.

Another advantage of the present invention lies in the fact that the above mentioned results can be obtained in a simple, easy for the user and extremely repetitive way.

In fact, the above described configurations are extremely simple to apply for anybody with a minimum knowledge of the human anatomy and the stimulation performed with the electrodes applied according thereto, give sure and lasting results.

It is to be understood that the above description is illustrative and not limitative, so that possible variations of the proposed method should be considered included in the scope of the invention, as described above and claimed in the following.

I claim:

1. A method for controlled stimulation of predetermined areas of a human body to improve physiological parameters in the body areas comprising:

providing a plurality of electrodes of positive electric polarity and a plurality of electrodes of negative electric polarity;

providing electric voltage for the positive electrodes and the negative electrodes, the voltage having a frequency and an intensity which are variable in a predetermined way;

arranging said positive electrodes and negative electrodes in peripheral positions of said body areas to be stimulated, and subsequently activating the positive and negative electrodes in a prefixed sequence, concentrating electromagnetic waves in said body areas;

arranging the positive electrodes substantially side by side, to first peripheral positions of said areas, these positions being closer to the heart, arranging the negative electrodes substantially side by side, to second peripheral positions of said areas, the second peripheral positions being farther from the heart.

2. The method of claim 1, wherein four positive electrodes are substantially arranged in a lower abdomen area, directly over the navel, forming a squashed semicircle with a convex part turned upwards, and four negative electrodes are substantially arranged in said lower abdomen area, directly over the pubis, forming a squashed semicircle with a convex part turned downwards.

3. The method of claim 1 wherein four positive electrodes are substantially arranged in an upper abdomen area, directly under the chest, forming a squashed semicircle with a convex part turned upwards, and four negative electrodes, substantially arranged in said abdomen area, directly over the navel forming a squashed semicircle with a convex part turned downwards.

4. The method of claim 1, further comprising arranging said positive electrodes and said negative electrodes vertically symmetrically around an abdomen area, applying said positive electrodes on the oblique rectus muscle joint, applying said negative electrodes on a lower part of the abdomen rectus muscles.

5. A method for controlled stimulation of predetermined areas of a human body to improve physiological parameters in the body areas comprising:
   providing a plurality of electrodes of positive electric polarity and a plurality of electrodes of negative electric polarity;
   providing electric voltage for the positive electrodes and the negative electrodes, the voltage having a frequency and an intensity which are variable in a predetermined way;
   arranging said positive electrodes and negative electrodes in peripheral positions of said body areas to be stimulated, and subsequently activating the positive and negative electrodes in a prefixed sequence, concentrating electromagnetic waves in said body areas;
   arranging the positive electrodes substantially side by side, to first peripheral positions of said areas, these positions being closer to the heart, arranging the negative electrodes substantially side by side, to second peripheral positions of said areas, the second peripheral positions being farther from the heart;
   arranging the positive electrodes and the negative electrodes around a gluteus area, applying a first positive electrode in a substantially central position, directly over the gluteus area, applying a second positive electrode next to the first positive electrode in an external part over the gluteus and applying a first negative electrode and a second negative electrode respectively, directly under said gluteus area.

6. The method of claim 5 wherein said second negative electrode is moved to an external part of the leg directly over the knee.

7. A method for controlled stimulation of predetermined areas of a human body to improve physiological parameters in the body areas comprising:
   providing a plurality of electrodes of positive electric polarity and a plurality of electrodes of negative electric polarity;
   providing electric voltage for the positive electrodes and the negative electrodes, the voltage having a frequency and an intensity which are variable in a predetermined way;
   arranging said positive electrodes and negative electrodes in peripheral positions of said body areas to be stimulated, and subsequently activating the positive and negative electrodes in a prefixed sequence, concentrating electromagnetic waves in said body areas;
   arranging four positive electrodes horizontally side by side directly over an external thigh area, arranging four negative electrodes horizontally side by side directly below said external thigh area.

8. A method for controlled stimulation of predetermined areas of a human body to improve physiological parameters in the body areas comprising:
   providing a plurality of electrodes of positive electric polarity and a plurality of electrodes of negative electric polarity;
   providing electric voltage for the positive electrodes and the negative electrodes, the voltage having a frequency and an intensity which are variable in a predetermined way;
   arranging said positive electrodes and negative electrodes in peripheral positions of said body areas to be stimulated, and subsequently activating the positive and negative electrodes in a prefixed sequence, concentrating electromagnetic waves in said body areas;
   arranging the positive electrodes and the negative electrodes to acupuncture indicated drain points.

9. The method of claim 8, further comprising applying a first positive electrode to an upper part of an internal thigh area and a second positive electrode to a lower part of an internal knee area, applying a first negative electrode to an upper part of said internal knee area and a second negative electrode to an internal part of the ankle.

10. The method of claim 8 further comprising applying a first pair of positive electrodes to the oblique rectus muscles joint, applying a first corresponding pair of negative electrodes symmetrically to a lower part of the abdomen rectus muscle, applying a second pair of positive electrodes to an upper part of each internal thigh area, and applying a second pair of negative electrodes to each internal knee area.

* * * * *